United States Patent [19]

Stopp et al.

[11] Patent Number: 4,529,817
[45] Date of Patent: Jul. 16, 1985

[54] PROCESS FOR PREPARING AROMATIC HYDROXYCARBOXYLIC ACIDS

[75] Inventors: Gerhard Stopp, Leverkusen; Horst Karkossa, Leichlingen; Viktor Trescher, Leverkusen, all of Fed. Rep. of Germany

[73] Assignee: Bayer Aktiengesellschaft, Leverkusen, Fed. Rep. of Germany

[21] Appl. No.: 472,470

[22] Filed: Mar. 7, 1983

[30] Foreign Application Priority Data

Mar. 23, 1982 [DE] Fed. Rep. of Germany ....... 3210599

[51] Int. Cl.$^3$ ............................................. C07L 51/15
[52] U.S. Cl. .................................. 562/423; 562/424; 562/425
[58] Field of Search ........................ 562/423, 424, 425

[56] References Cited

U.S. PATENT DOCUMENTS 4,287,357  9/1981  Mueller ............................... 562/425

*Primary Examiner*—Paul J. Killos
*Attorney, Agent, or Firm*—Sprung, Horn, Kramer & Woods

[57] ABSTRACT

Aromatic hydroxycarboxylic acids are prepared by reacting an alkali metal salt of an aromatic hydroxy compound in solid phase with carbon dioxide, by reacting an alkali metal salt of an aromatic hydroxy compound in the form of granules in a fluidized bed with carbon dioxide, if desired under elevated pressure, at first at temperatures of 20° to 130° C. until at least 40% of the hydroxy compound has been converted into the corresponding carbonate, then completing the reaction at temperatures of 135° to 300° C., and then converting the reaction product obtained into the free acid.

15 Claims, No Drawings

PROCESS FOR PREPARING AROMATIC HYDROXYCARBOXYLIC ACIDS

The invention relates to a process for preparing aromatic hydroxycarboxylic acids by reacting an alkali metal salt of an aromatic hydroxy compound in solid phase with carbon dioxide.

CROSS REFERENCE TO RELATED APPLICATION

This application is related to one filed concurrently herewith entitled Process for the Preparation of Aromatic Hydroxycarboxylic Acids assigned to the assignees hereof.

The reaction of alkali metal salts of aromatic hydroxy compounds in solid form with the aid of carbon dioxide to give the alkali metal salts of the corresponding aromatic hydroxycarboxylic acids is known. Thus, for example, German Pat. No. 960,206 claims a process for converting fine-grained alkali metal salts of aromatic monohydroxy compounds into the alkali metal salts of the corresponding hydroxycarboxylic acids with the aid of carbon dioxide, which is characterized in that the starting salts are used in the form of particles having a diameter of 20 to 200 μm and are treated in a fluid-like state, a so-called fluidized bed, with carbon dioxide gas.

It is also known, from German Auslegeschrift No. 1,493,881, to prepare p-hydroxybenzoic acid by reaction of potassium phenolate at a temperature of 190° to 210° C. and under a pressure of up to 6 atmospheres gauge using a cycle brought to the reaction temperature and consisting of carbon dioxide and inert gas, the heat of reaction being continually dissipated, the phenol being formed being taken care of, and consumed carbon dioxide being replaced by fresh gas and potassium phenolate being used in the form of anhydrous granules or pellets having a diameter or edge length of up to 30 mm. In this process, the reaction takes place in a fixed-bed reactor charged with the potassium phenolate and in which the gas is passed upwards.

British Pat. No. 1,205,447 describes a process for preparing alkali metal salts of aromatic hydroxycarboxylic acids by reacting carbon dioxide at an elevated temperature with pulverulent alkali metal phenolates which have a diameter of less than 70 μm.

It is also known, from German Offenlegungsschrift No. 2,926,694 (U.S. Pat. No. 4,171,353), to carbonize a dry alkali metal phenolate in solid phase with carbon dioxide under pressure to give the alkali metal carboxylate or the corresponding phenol. In this process, carbon dioxide is reacted in the first stage with finely divided solid alkali metal phenolate at a temperature below 135° C. until at least 25% of the stochiometric amount of carbon dioxide have been absorbed by the phenolate, and the carbonization of the phenolate is continued in the second stage by increasing the temperature to above 135° C.

The processes known from the state of the art suffer from the disadvantage of, on occasion, unsatisfactory yields in aromatic hydroxycarboxylic acids (German Offenlegunsschrift No. 2,926,694, German Auslegeschrift No. 1,493,881 and British No. 1,205,447), and the problems which arise on using a pulverulent starting product, such as the handling of the pulverulent material which, for safety reasons, is associated with great technical effort (German No. 960,206, British No. 1,205,447 and German Offenlegungsschrift No. 2,926,694). A further disadvantage is that under the conditions described in German No. 960,206 the fluidized bed is considerably interfered with through tackiness due to the presence of liquid phenol, a fact which cannot be adequately prevented even by adding porous substances, such as kaolin.

A process has now been found for preparing aromatic hydroxycarboxylic acids by reacting alkali metal salts of aromatic hydroxy compounds in solid phase with carbon dioxide, which is characterized in that the alkali metal salts of aromatic hydroxy compounds are reacted in the form of granules in a fluidized bed with carbon dioxide at first at temperatures of 20° to 130° C. until at least 40% of the hydroxy compound has been converted into the corresponding carbonate, the reaction is then completed at temperatures of 135° to 300° C., and the rection product obtained is than converted into the free acid. The reaction at 20° to 130° C. and/or the reaction at 135° to 300° C. can be carried out under pressure. The free acid can be obtained from the alkalisalt of the hydroxycarboxylic acid in the customary manner.

The alkali metal salts of aromatic hydroxy compounds which can be used in the process according to the invention are the sodium and/or potassium salts of phenol, of cresols, of naphthols, of 2-hydroxycarbazole or of 3-hydroxydiphenylene oxide. The aromatic hydroxy compounds can be monosubstituted or polysubstituted by lower alkyl, such as methyl, ethyl or tert.-butyl, and by halogens, such as fluorine, chlorine or bromine, preferably chlorine. Sodium phenolate, the sodium salts of cresols and the sodium salts of chlorophenols, in particular sodium phenolate, are preferably used in the process according to the invention.

The alkali metal salts of the aromatic hydroxy compounds are employed in the process according to the invention in the form of anhydrous granules having a diameter of about 0.2 to 5 mm, preferably 0.3 to 4 mm, and an internal surface area of 1 to 6, preferably 2 to 4, $m^2$ per g of granules (surface area determined by the BET method/DIN 66,132).

The granules to be used according to the invention can be prepared using an own, earlier process, which is described in the disclosure of which is hereby incorporated herein by reference.

In the process according to the invention, the granulated salts of the aromatic hydroxy compounds are reacted in a fluidized bed with carbon dioxide which can, if desired, also contain inert gas, such as nitrogen. In this process, the carbon dioxide is passed in a cycle, with the heat of reaction being conducted away. The carbon dioxide being cycled is replenished by the amount of carbon dioxide which has been consumed during the reaction.

According to the invention, the reaction is carried out in the fluidized bed first at temperatures of about 20° to 130° C., preferably at 70° to 120° C., particularly preferably at 80° to 100° C. The pressures in this reaction are 1 to 50, preferably 2 to 10, particularly preferably 3 to 8, bar absolute.

When about 40%, preferably 50 to 80%, of the aromatic hydroxy compound has reacted with the carbon dioxide to give the corresponding carbonate, the temperature is increased to about 135° to 300° C., preferably 140° to 210° C., depending on which alkali metal salt of the aromatic hydroxy compound is being used, and the reaction is completed in the presence of carbon dioxide under pressures of about 1 to 50 bar absolute, preferably 3 to 6 bar absolute.

This further reaction can advantageously also be carried out separately in another apparatus, such as a stirred vessel or a screw machine, if desired with the additon of small amounts of the corresponding aromatic hydroxy compound (about 5 to 20 mol %, relative to the salt used).

In an advantageous embodiment of the process according to the invention, for example in preparing salicylic acid from sodium phenolate, the reaction mixture obtained in the further reaction is then also heat-treated at elevated temperatures (about 180° to 300° C.) which, again, depend on the alkali metal salt of the aromatic hydroxy compound used.

To work up the reaction mixture, excess aromatic hydroxy compound is first distilled off in vacuo if desired. Water is then added to the reaction mixture, the mixture is neutralized, if desired, and clarified by additives, such as activated carbon, and the free hydroxycarboxylic acid is then precipitated by means of mineral acids, such as hydrochloric acid or sulphuric acid.

The process according to the invention can be carried out as follows (demonstrated with the example of the preparation of salicylic acid):

Dry and granulated sodium phenolate is continuously supplied to the fluidized-bed reactor and is reacted at about 70° to 90° C. under a pressure of about 4 to 6 bar absolute with carbon dioxide, which serves as fluidizing gas and is passed in a cycle. While this total pressure is being maintained, the cycling gas is replenished by the amount of carbon dioxide which has been consumed in the reaction with the hydroxy compound. When the sodium phenolate has reacted to an extent of about 70% by absorption of carbon dioxide to sodium phenyl carbonate, the carbonate is transferred to a stirred vessel and further reacted there with carbon dioxide and with the addition of phenol at temperatures of about 160° to 170° C. and under a pressure of about 5.5 to 6.5 bar absolute to give sodium salicylate. In a further reaction at about 190° to 200° C. and under a pressure of about 5.5 bar absolute, the sodium salt of p-hydroxybenzoic acid, which is formed in small amounts in the reaction, is converted into the sodium salt of salicylic acid. Residual amounts of phenol are removed from the reaction mixture in a subsequent vacuum distillation, and the reaction mixture is then dissolved in water, the solution is neutralized and clarified by means of activated carbon, and sulphuric acid is used to precipitate free salicylic acid.

The process according to the invention can be carried out not only continuously but also discontinuously. It is advantageously carried out continuously.

The yields of aromatic hydroxycarboxylic acids obtained in the process according to the invention vary with the salt of the aromatic hydroxy compound used between about 85 to 96% of theory, relative to the starting compound.

The advantages of the process according to the invention must be considered to be, in particular, the avoidance of local superheating, whereby phenol formation, which would lead to caking and stickiness, is prevented. The result is that considerably shortened reaction times are achieved with a low amount of energy consumed. Exact temperature control provides the possibility of minimizing the formation of by-products. In addition, the process according to the invention makes it possible to avoid the reaction products becoming discoloured due to oxidation by air. Finally, the process according to the invention produces the aromatic hydroxycarboxylic acids in high yields and with a high selectivity.

It is particularly surprising in the process according to the invention that granules treated in the fluidized bed are preserved in this form even after the reaction with carbon dioxide and can thus be removed from the fluidized-bed reactor without problems. The granule form is also retained when the reaction is completed at an elevated temperature, a fact which is particularly favourable for carrying out the process according to the invention in industry and for the further processing of the reaction products. It is also surprising that there is no impairment of the rate of the reaction and the yield despite the fact that the alkali metal salts of the aromatic hydroxy compounds used are coarse-grained, although it is pointed out in Indian J. Technol. volume 11, page 187 (1973) that the reaction rate of the carboxylation decreases with increasing particle size of sodium phenolate.

The aromatic hydroxycarboxylic acids prepared using the process according to the invention are valuable intermediate products for preparing dyestuffs, medicaments, plant protection agents, tanning materials and cosmetics (Ullmanns Encyclo. d. techn. Chemie [Ullmann's Encyclopedia of Industrial Chemistry], volume 13, (4th edition), pages 163–168).

The examples which follow are intended to illustrate the process according to the invention without, however, restricting it to these examples.

EXAMPLE 1

A continuous stream of dry sodium phenolate in granulated form (main fraction: 0.5–1.5 mm diameter) is added at a rate of 8 parts/hour via a suitable adding device to a fluidized bed. Carbon dioxide is used as the fluidizing gas and it is, at the same time, the reaction gas. The reaction gas is cycled and maintained under a constant pressure of 5.5 bar absolute. The gas absorbs the heat of reaction and, after leaving the fluidized bed, is cooled down in a heat exchanger in such a way that a constant temperature of 90° C. is maintained in the fluidized bed. About 0.7 mol of carbon dioxide are absorbed per mol of sodium phenolate (conversion of aromatic hydroxy compound: 70%). 10 parts of the reaction product are removed per hour in a constant stream from the fluidised bed with a residence time of about 20 minutes. This product, which has retained its original granulated form, continuously flows alternately into one of two vessels which are equipped with a simple stirring deivce and which is under a carbon dioxide pressure of 5.4 bar absolute. A temperature of 160° C. is first maintained in this vessel until the vessel is filled to 85% with granules. The feed is then switched to the second stirred vessel. 10–15 mol % of phenol (relative to the sodium phenolate used) are injected with stirring in the course of 1 hour into the first vessel and absorbed by the granules. The contents of the reactor are heated to 210° C. under a carbon dioxide pressure of 5.4 bar absolute and maintained at this temperature for 1 hour. The pressure is then let down, and excess phenol is distilled off in vacuo. Below 150° C., the interior of the vessel is flooded with water. The dissolved sodium salicylate is converted in a known manner into the free salicylic acid, by acidifying with mineral acid. The yield of salicylic acid is 94%, relative to alkali used.

EXAMPLE 2

A continuous stream of dry and granulated potassium 2-naphtholate is added at a rate of 5 parts/hour to a fluidized bed. The fluidizing gas used is carbon dioxide, which is cycled and maintained under a constant pressure of 5.5 bar. Carbon dioxide consumed by the reaction is replenished by maintaining the pressure at a constant value. A constant temperature of about 80° C. is maintained in the fluidized bed by cooling down the cycling gas in a heat exchanger. About 0.5 mol of carbon dioxide are consumed per mol of naphtholate (conversion: 50%) at a residence time of about 5 minutes. A continuous stream of reaction product is removed from the fluidized bed at a rate of 5.6 parts/hour, the original granulated form being retained during the reaction.

The reaction product is converted in a stirred vessel at 80° to 150° C. under a carbon dioxide pressure of 5.0 bar absolute to give potassium 2-hydroxynaphthalene-1-carboxylate. The yield is over 95%, relative to alkali used.

The reaction product is very pure and can be further processed directly as an intermediate product, or it is dissolved in water in a customary manner, clarified under neutral conditions, and converted with mineral acids into the free acid.

What is claimed is:

1. In a process for preparing aromatic hydroxycarboxylic acid by contacting an alkali metal salt of an aromatic hydroxy compound in the solid phase with carbon dioxide, and thereafter converting the reaction product into the free acid, the improvement which comprises:
    (a) reacting said alkali metal salt of said aromatic hydroxy compound in the form of granules with carbon dioxide in a fluidized bed at a temperature of 20°–130° C. until at least 40% of the alkali metal salt of an aromatic hydroxy compound has been converted into the corresponding carbonate; and wherein the reaction mixture consists essentially of said alkali metal salt of an aromatic hydroxy compound in the solid phase and said carbon dioxide
    (b) thereafter increasing the temperature of the reaction to 135°–300° C. and completing the reacting at such temperature.

2. Process according to claim 1 wherein the reaction is completed in a fluidized bed.

3. Process according to claim 1 wherein the alkali metal salt of an aromatic hydroxy compound is a sodium and/or potassium salt of phenol, a cresol, a naphthol, 2-hydroxycarbazole or 3-hydroxydiphenylene oxide.

4. Process according to claim 1 wherein said alkali metal salt of an aromatic hydroxy compound is in the form of a granule having a diameter of 0.2 to 5 mm, and an internal surface area of 1 to 6 m$^2$ per gram.

5. Process according to claim 1 wherein the reaction at 20°–130° C. is carried out under pressure.

6. Process according to claim 1 wherein the process is carried out under a pressure 1–50 bars absolute.

7. Process according to claim 1 wherein the alkali metals salt of an aromatic hydroxy compound is reacted with carbon dioxide in a fluidized bed at temperature of 70°–120° C.

8. Process according to claim 1 wherein the reaction of said alkali metals salt of an aromatic hydroxy compound with carbon dioxide is carried out until 50–80% of said alkali metal salt of an aromatic hydroxy compound has been converted to the corresponding carbonate.

9. Process according to claim 1 wherein the reaction wherein the process is completed at a temperature of 140°–210° C.

10. A process according to claim 1 wherein said salt is sodium phenolate.

11. A process according to claim 1 wherein said salt is potassium-2-naphtholate.

12. A process according to claim 10 wherein step A is effected at a temperature of 70° to 90° C. at 4–6 bars absolute carbon dioxide pressure.

13. A process according to claim 12 wherein step B is effected at a temperature of 160° to 170° C. at a pressure of 5.5–6.5 bars absolute carbon dioxide pressure.

14. A process according to claim 10 wherein step A is effected at a temperature of 70° to 120° C. at 1–50 bars absolute carbon dioxide pressure.

15. A process according to claim 14 wherein step B is effected at a temperature of 80° to 150° C.

* * * * *